United States Patent
Sotomayor et al.

(10) Patent No.: US 10,016,421 B2
(45) Date of Patent: Jul. 10, 2018

(54) HISTONE DEACETYLASE 6 INHIBITION FOR ENHANCING T-CELL FUNCTION DURING ANTI-TUMOR RESPONSE AND TUMOR-PEPTIDE VACCINATION

(71) Applicant: H. LEE MOFFITT CANCER CENTER AND RESEARCH INSTITUTE, INC., Tampa, FL (US)

(72) Inventors: Eduardo M. Sotomayor, Tampa, FL (US); Alejandro V. Villagra, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 15/120,053

(22) PCT Filed: Apr. 6, 2015

(86) PCT No.: PCT/US2015/024463
§ 371 (c)(1),
(2) Date: Aug. 18, 2016

(87) PCT Pub. No.: WO2015/154065
PCT Pub. Date: Oct. 8, 2015

(65) Prior Publication Data
US 2017/0056402 A1    Mar. 2, 2017

Related U.S. Application Data

(60) Provisional application No. 62/085,878, filed on Dec. 1, 2014, provisional application No. 61/975,811, filed on Apr. 5, 2014.

(51) Int. Cl.
| | |
|---|---|
| A61K 31/505 | (2006.01) |
| A61K 39/00 | (2006.01) |
| A61K 45/06 | (2006.01) |
| A61K 31/17 | (2006.01) |
| A61K 31/416 | (2006.01) |
| A61K 31/422 | (2006.01) |
| A61K 31/437 | (2006.01) |
| A61K 31/454 | (2006.01) |
| A61K 31/69 | (2006.01) |
| C12N 5/0783 | (2010.01) |
| A61K 39/395 | (2006.01) |

(52) U.S. Cl.
CPC ............ *A61K 31/505* (2013.01); *A61K 31/17* (2013.01); *A61K 31/416* (2013.01); *A61K 31/422* (2013.01); *A61K 31/437* (2013.01); *A61K 31/454* (2013.01); *A61K 31/69* (2013.01); *A61K 39/0011* (2013.01); *A61K 39/3955* (2013.01); *A61K 45/06* (2013.01); *C12N 5/0636* (2013.01); *C12N 5/0638* (2013.01); *A61K 2039/5158* (2013.01); *A61K 2039/545* (2013.01); *A61K 2039/55511* (2013.01); *A61K 2039/57* (2013.01); *A61K 2039/585* (2013.01); *C12N 2501/065* (2013.01); *C12N 2501/2302* (2013.01)

(58) Field of Classification Search
None
See application file for complete search history.

(56) References Cited

U.S. PATENT DOCUMENTS

| | | | |
|---|---|---|---|
| 9,409,858 B2 * | 8/2016 | Sotomayor | ........ A61K 31/506 |
| 2007/0190022 A1 | 8/2007 | Bacopoulos et al. | |
| 2012/0270818 A1 * | 10/2012 | Marks | ........ A61K 31/167 514/27 |

FOREIGN PATENT DOCUMENTS

WO    2013/134467 A1    9/2013

OTHER PUBLICATIONS

Lindsey, WB, et al. "CD69 expression as an index of T-cell function: assay standardization, validation and use in monitoring immune recovery", Cytotherapy, 2007, vol. 9, No. 2, pp. 123-132: p. 123, Methods and Results.
International Search Report and Written Opinion issued in related International Application No. PCT/US2015/024463 dated Jul. 31, 2015.
De Zoeten EF, et al (2011). Histone deacetylase 6 and heat shock protein 90 control the functions of Foxp3(+) T-regulatory cells. Mol Cell Biol 31(10):2066-78.

* cited by examiner

*Primary Examiner* — Heidi Reese
(74) *Attorney, Agent, or Firm* — Meunier Carlin & Curfman LLC

(57) ABSTRACT

Disclosed are methods whereby an effective amount of a HDAC6 inhibitor is used to activate a subjects T-cell response to tumor or tumor vaccine. Methods of using HDAC6 inhibitors to increase a subjects anti-tumor immune response, alone or in conjunction with other tumor treatments, are also disclosed.

14 Claims, 16 Drawing Sheets

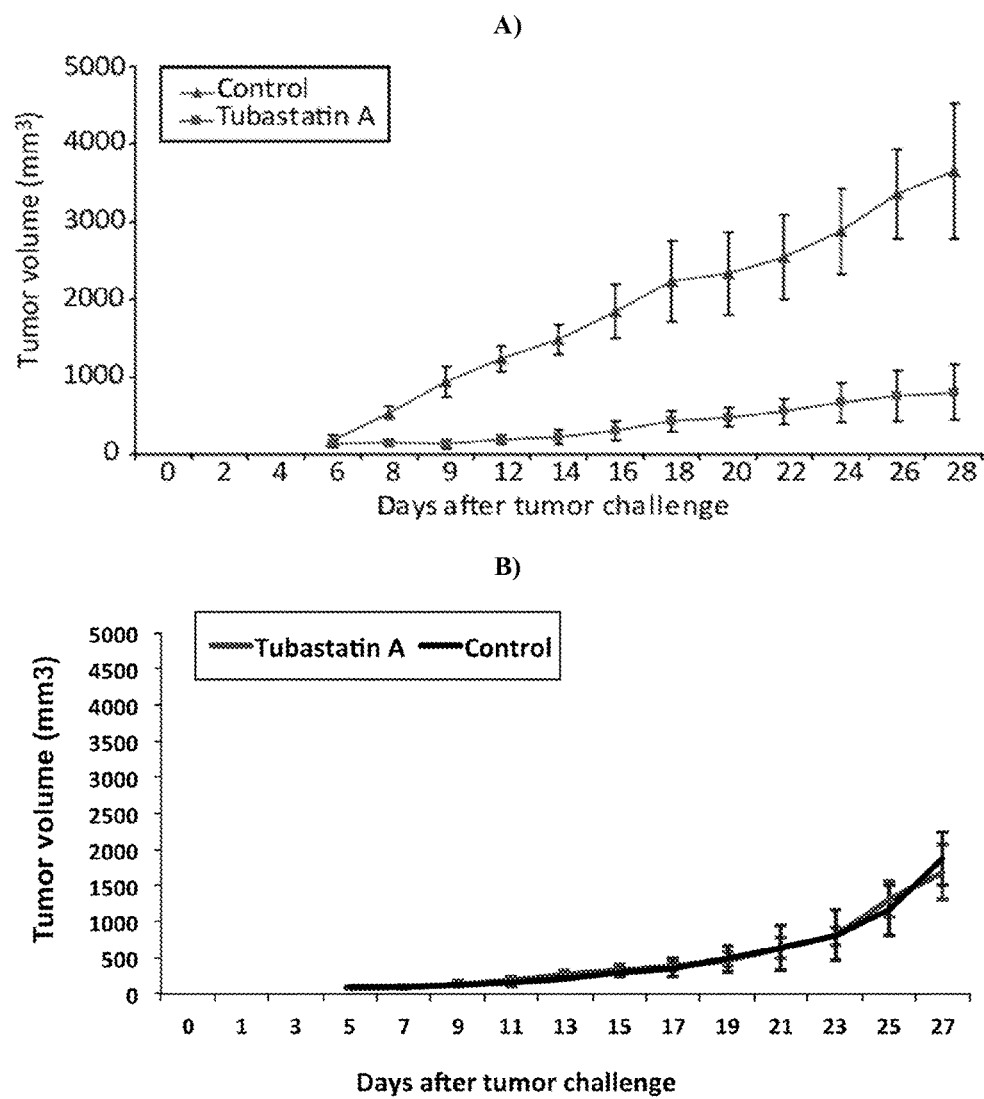
FIGs. 3A-B

HISTONE DEACETYLASE 6 INHIBITION FOR ENHANCING T-CELL FUNCTION DURING ANTI-TUMOR RESPONSE AND TUMOR-PEPTIDE VACCINATION

CROSS-REFERENCE TO RELATED APPLICATIONS

This application claims benefit of U.S. Provisional Application No. 61/975,811, filed Apr. 5, 2014, and Application Ser. No. 62/085,878, filed Dec. 1, 2014, which are hereby incorporated herein by reference in their entirety.

ACKNOWLEDGMENT OF GOVERNMENT SUPPORT

This invention was made with government support under Grant number CA134807 awarded by the National Institutes of Health. The government has certain rights in this invention.

BACKGROUND

Histone deacetylases (HDACs) are a family of epigenetic regulators with emerging roles in both tumor and immune system biology. HDAC6 is a 131 KDa protein considered to be a key regulator of cytoskeleton dynamics and cell-cell interactions (Hubbert et al. Nature 417:455-458 (2002); Valenzuela-Fernandez, et al. Trends in Cell Biology 18:291-297 (2008)). Although this HDAC is predominantly cytoplasmic, studies have demonstrated its presence in nuclear extracts and its recruitment to gene promoter regions (Toropainen et al., J Mol Biol. 400:284-294 (2010)). HDAC6 has been reported to be over-expressed in several cancer types, including ovarian cancer, prostate cancer and acute myeloid leukemia (AML) (Aldana-Masangkay et al., J Biomed Biotechnol 2011:875824 (2010)).

HDAC6 has been implicated in the modulation of immune responses (Serrador et al., Immunity 20:417-428 (2004); Kalin et al., J Med Chem. (2012)). Recently, HDAC6 has been reported to modulate the acetylation of HSP90, a regulator of regulatory T-cell (Treg) suppressive activity (de Zoeten et al., Mol Cell Biol 31(10):2066-2078 (2011)). The use of HDAC6 as a target for generating and maintaining anti-tumor and peptide vaccination responses in vivo would be desirable. The subject matter disclosed herein addresses these desires and provide methods of targeting HDAC6 to improve immunotherapies.

SUMMARY

In accordance with the purposes of the disclosed materials, compounds, compositions, articles, devices, and methods, as embodied and broadly described herein, the disclosed subject matter relates to compositions and methods of making and using the compositions. In other aspects, the disclosed subject matter relates to the use of compounds having activity as HDAC6 inhibitors. For example, disclosed herein are methods whereby an effective amount of a HDAC6 inhibitor to activate the subject's T-cell response to tumor or tumor vaccine is administered to a subject having an oncological disorder, for example melanoma, and who is in need of treatment thereof. Methods of using HDAC6 inhibitors to increase a subject's anti-tumor immune response, alone or in conjunction with other tumor treatments, are also disclosed. In some embodiments, the HDAC6 inhibitors include ACY-1215, Tubacin, Tubastatin A, ST-3-06, ST-2-92, Nexturastat A, and Nexturastat B.

Additional advantages of the disclosed subject matter will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying figures, which are incorporated in and constitute a part of this specification, illustrate several aspects described below.

FIG. 3. Enhanced anti-tumor response promoted by HDAC6 inhibition is dependent on an intact immune system. (A) C57BL/6 or (B) SCID mice were subcutaneous injected with $3 \times 10^6$ Fc-muMCL1 lymphoma cells. After tumor appearance, six mice were treated daily with 35 mg/kg of Tubastatin A and four mice received vehicle control, for 16 days.

DETAILED DESCRIPTION

Figure 1A:
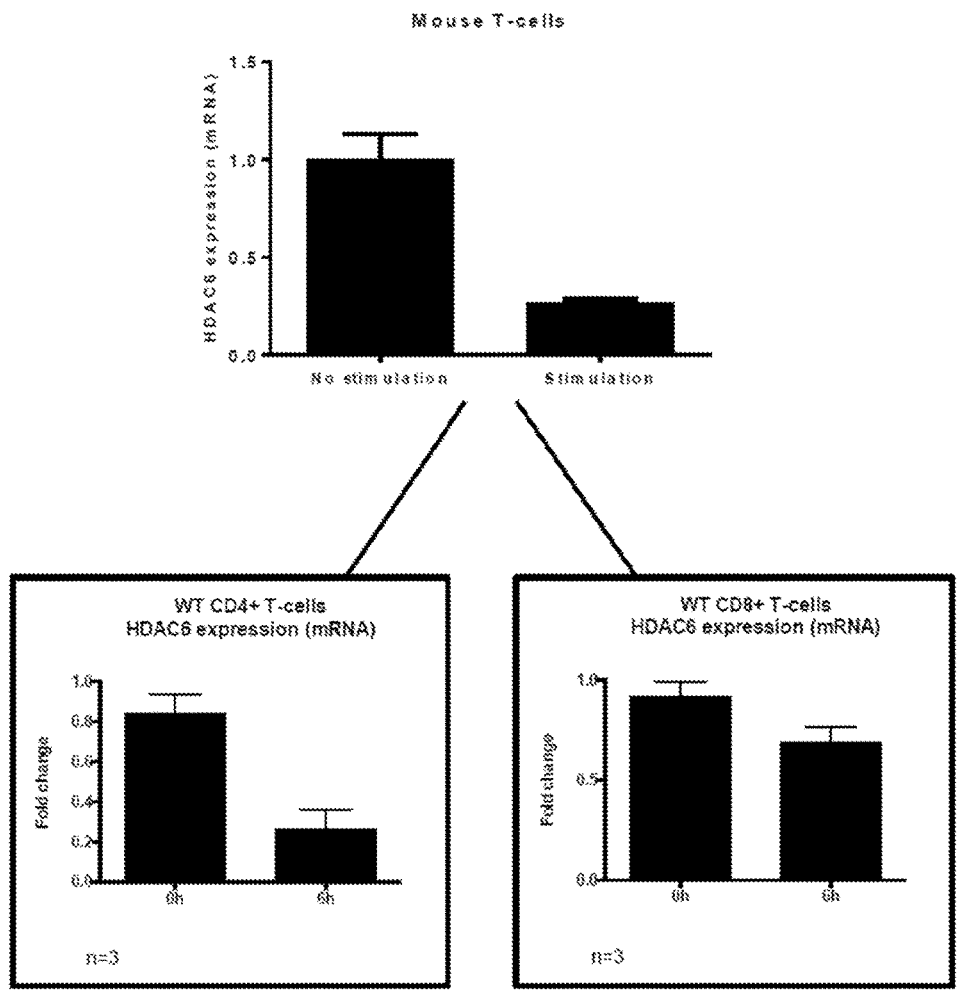
FIG. 1. HDAC6 expression is decreased after T-cell activation. CD3+ T-cells were isolated from (a) C57BL/6 mice lymph nodes or (b) peripheral blood of healthy human donors. Cells were plated and stimulated with anti-CD3/CD28 Dynabeads for 6 hours. Cells were lysed and HDAC6 mRNA expression was determined by qRT-PCR.
Figure 1B:
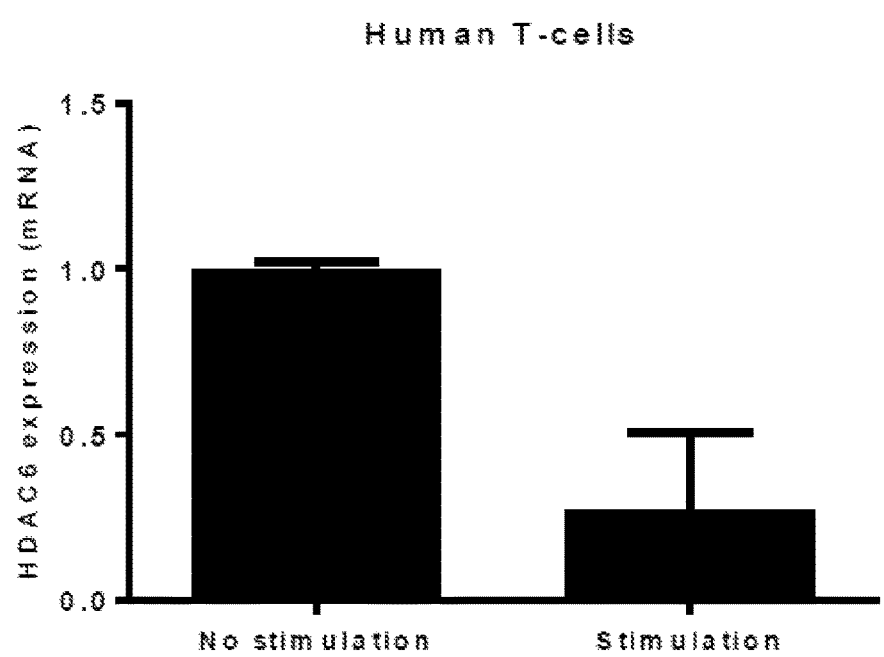
Figure 2A:
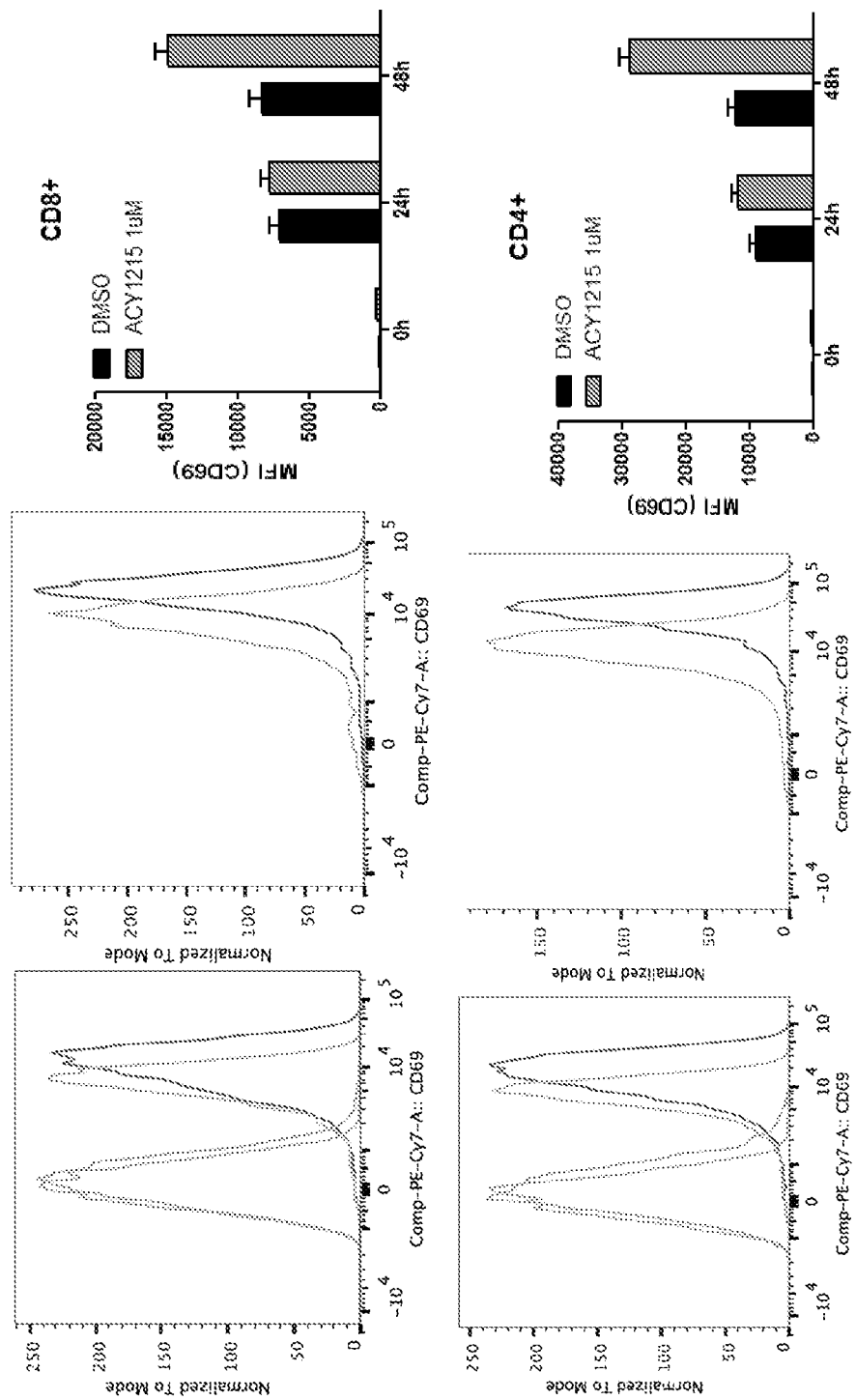
FIG. 2. HDAC6 inhibition leads to enhanced and maintained CD69 expression after activation. (A) CD3+ T-cells were isolated from C57BL/6 mice lymph nodes and activated via CD3/CD28 stimulation for 24 or 48 hours. Four mice were used per group; representative histograms are shown. (B) The human CD4+ cell line Jurkat was activated with PMA and Ionomycin for 24 hours. Cells were treated with ACY-1215 1 µM or DMSO control at the same time of activation and analyzed by flow cytometry for CD69 expression. Graphs represent values of mean fluorescence intensity (MFI).
Figure 2B:
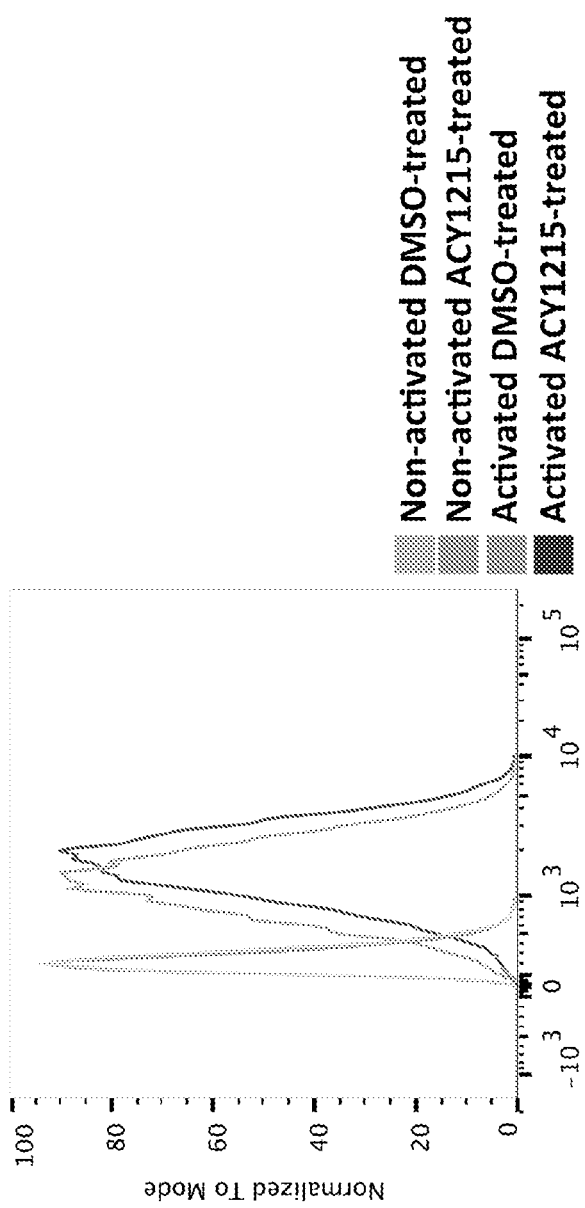
Figure 4A:
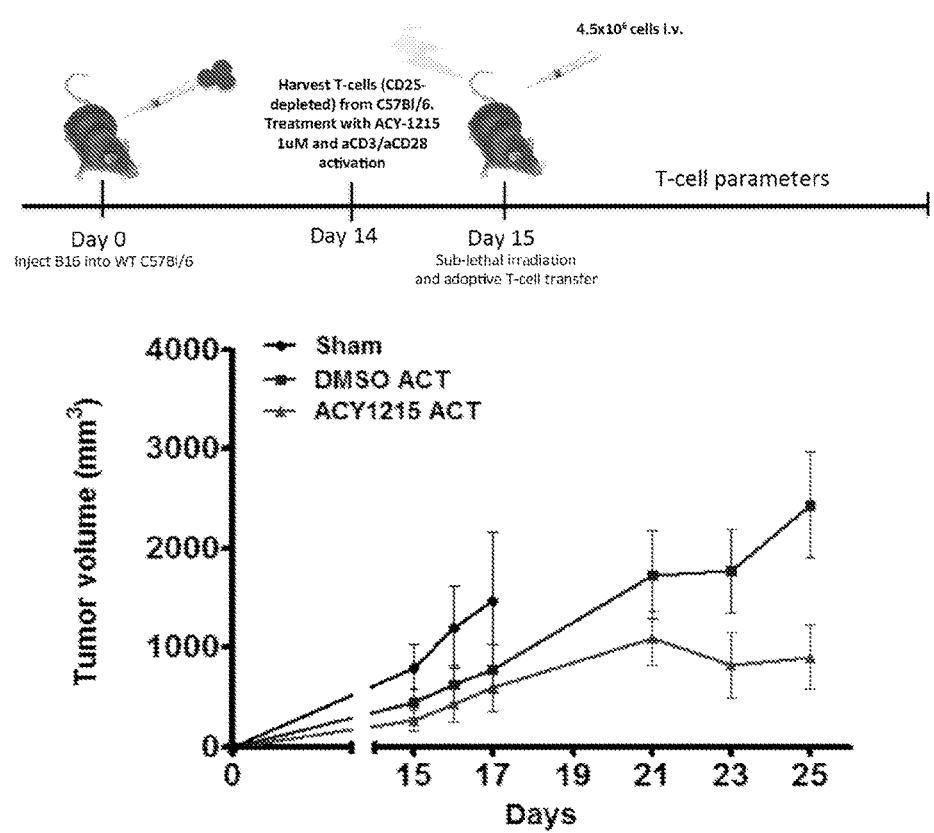
FIG. 4. HDAC6 inhibition in T-cells improves the anti-tumor response and results in a minor accumulation of central memory T-cells in the lymph nodes. CD3+ T-cells were isolated from C57BL/6 mice and depleted for CD25+ cells. Cells were activated via CD3/CD28 stimulation and treated concomitantly with ACY-1215 1 µM or DMSO control. Groups of five mice each were sub-lethally irradiated (600 rads) prior to adoptive transfer of $5.5 \times 10^6$ DMSO or ACY1215-treated T-cells via tail vein injection. (A) Tumor volume was assessed by caliper measurement. (B) Lymph nodes were harvested ten days after adoptive T-cell transfer and cells were analyzed by flow cytometry for T-cell memory markers.
Figure 4B:
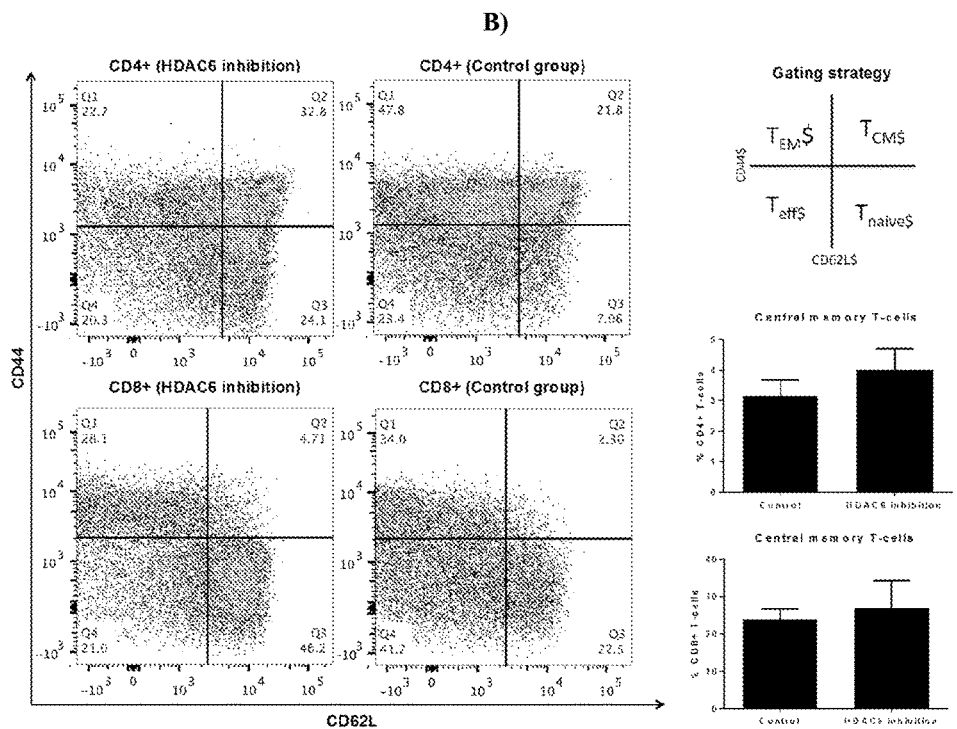
Figure 5A:
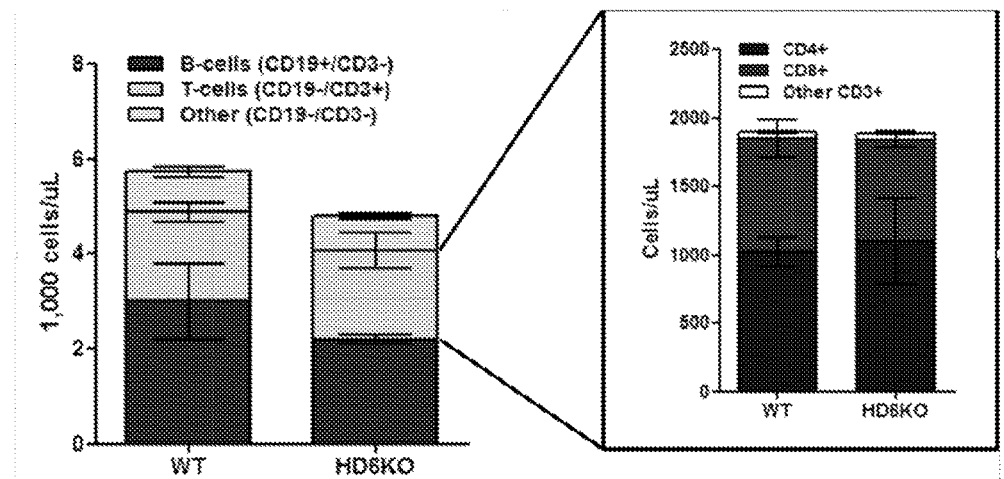
FIG. 5. Characterization of HDAC6KO mice lymphocyte compartments. Peripheral blood from C57BL/6 or HDAC6KO mice was analyzed by (A) complete blood count and (B) flow cytometry for lymphocyte markers. Three mice were used per group; representative plots are shown.
Figure 5B:
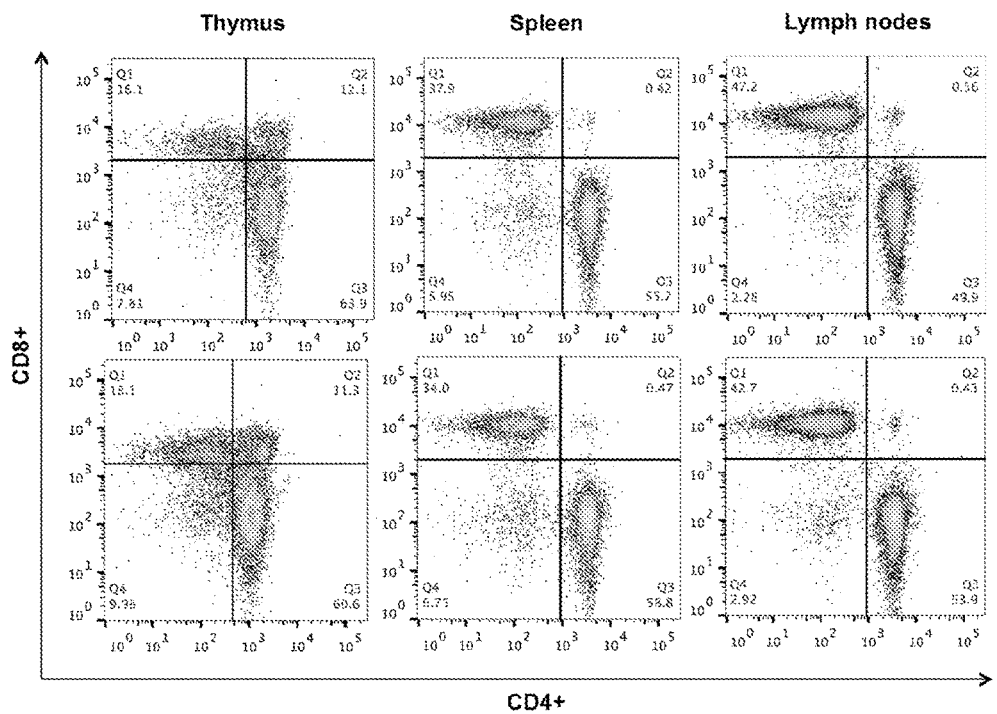
Figure 6:
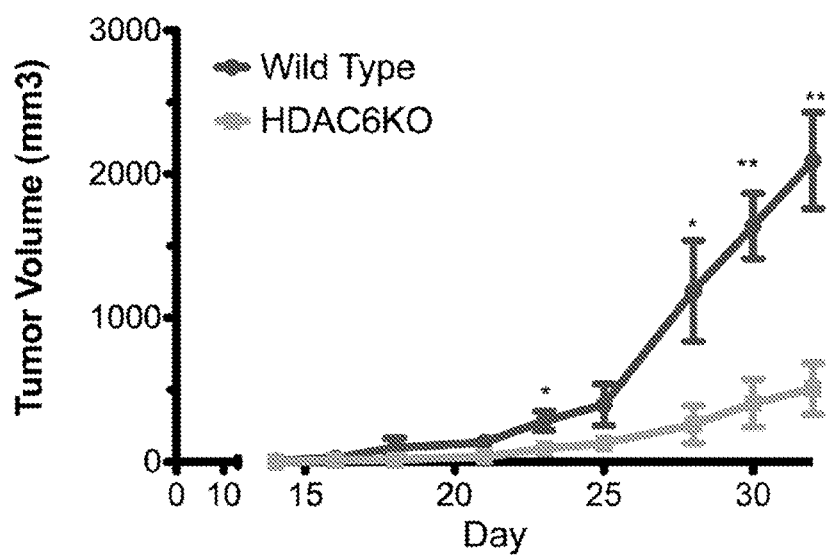
FIG. 6. HDAC6KO mice have reduced tumor growth. HDAC6KO and C57BL/6 mice were subcutaneous injected with $10^5$ B16-F10 melanoma cells. Tumor volume was calculated as indicated by the formula $(width)^2 \times length/2$.
Figure 7:
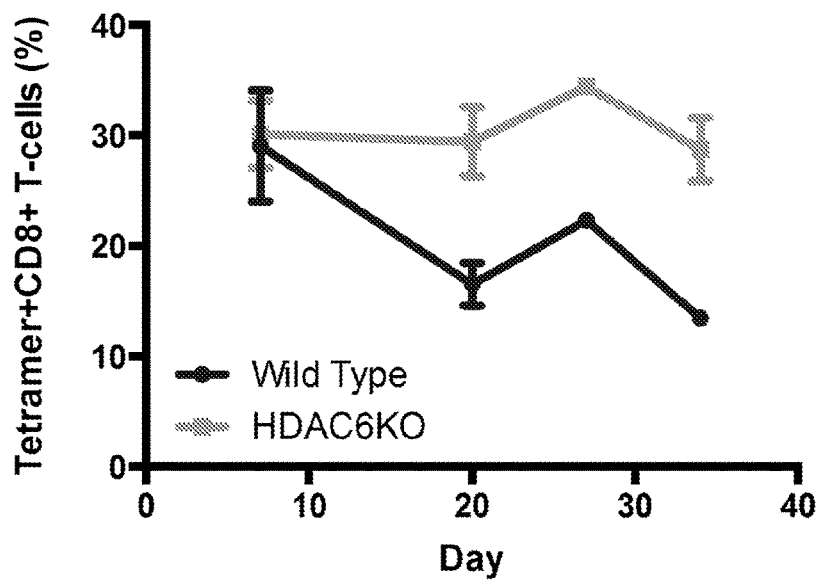
FIG. 7. HDAC6KO mice display a reduced contraction phase in the antigen-specific CD8+ T-cell compartment after tumor-peptide vaccination. HDAC6KO and wild-type mice received intravenous injections of a peptide vaccine containing Pam2-Trp1/455 peptide, Polyinosine-polycytidylic acid and anti-CD40, followed by a vaccination boost after 13 days. Graph represents the percentage of tetramer-specific CD8+ T-cells from peripheral blood collected on the indicated days.
Figure 8A:
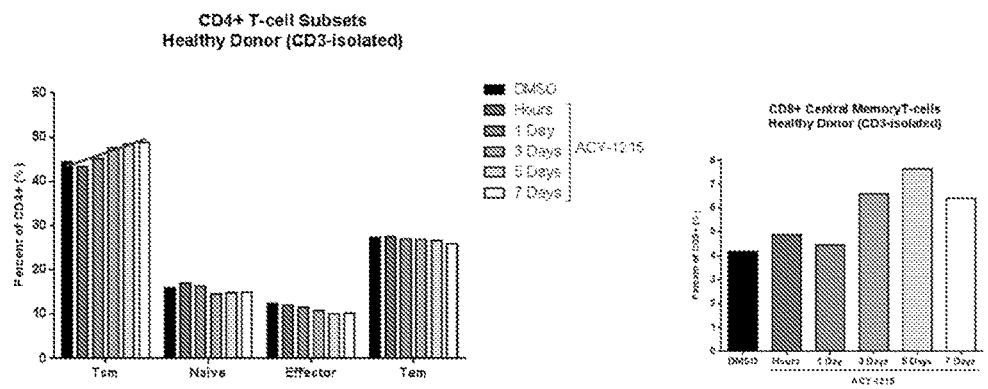
FIG. 8. HDAC6-selective inhibition increases central memory phenotype and cytolytic capacity of human T-cells. CD3+ T-cells were isolated from peripheral blood (PBMC) of healthy human donors and cultured in the presence of IL-2. (a) T-cells were treated once with ACY-1215 and analyzed by flow cytometry for the memory markers CD45RO and CD62L at days 7, 5, 3, 1 or 4 hours after treatment. (b-c) Cells from PBMC were treated once with ACY-1215 and stimulated with aCD3/CD28 Dynabeads for 72 hours. CD8+ T-cells were evaluated for the expression of IFNg and CD107a by flow cytometry.
Figure 8B:
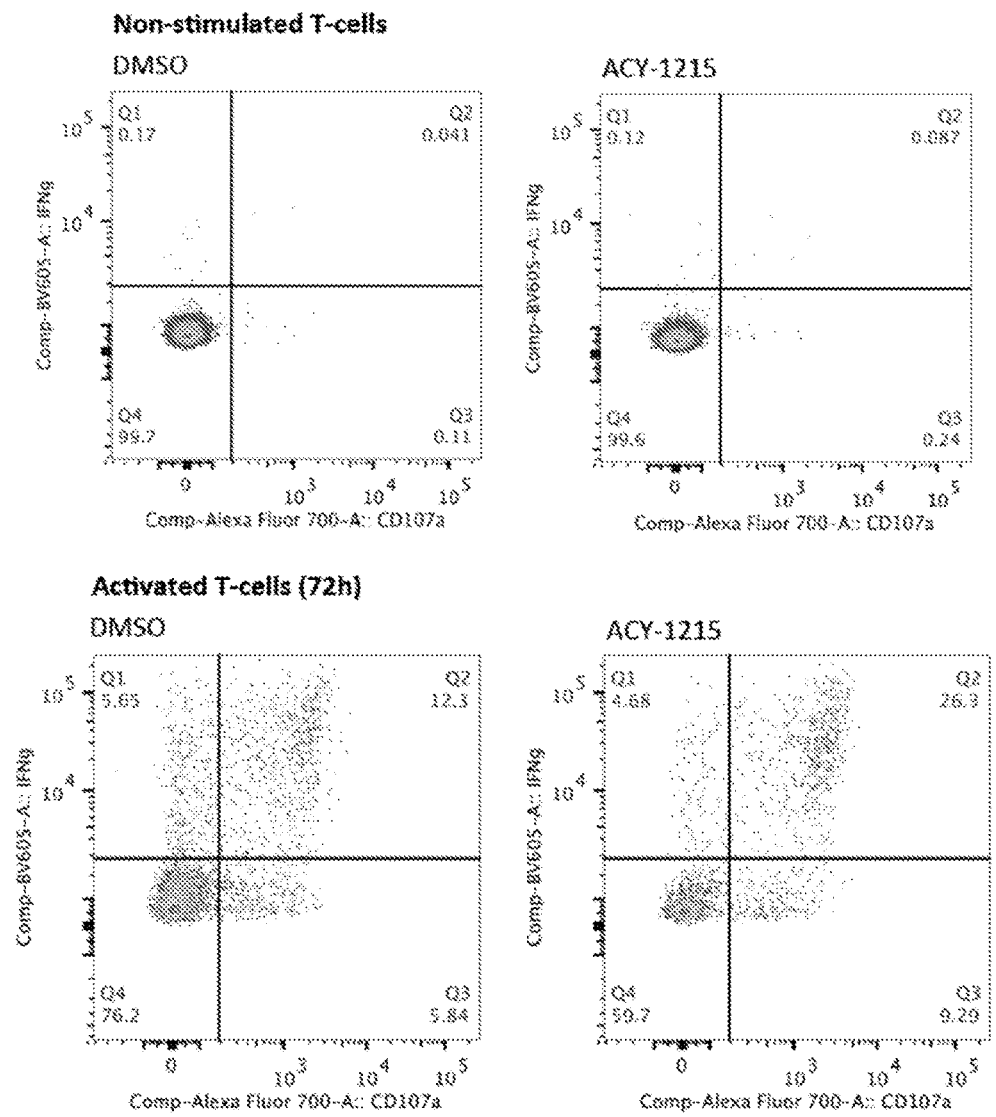
Figure 8C:
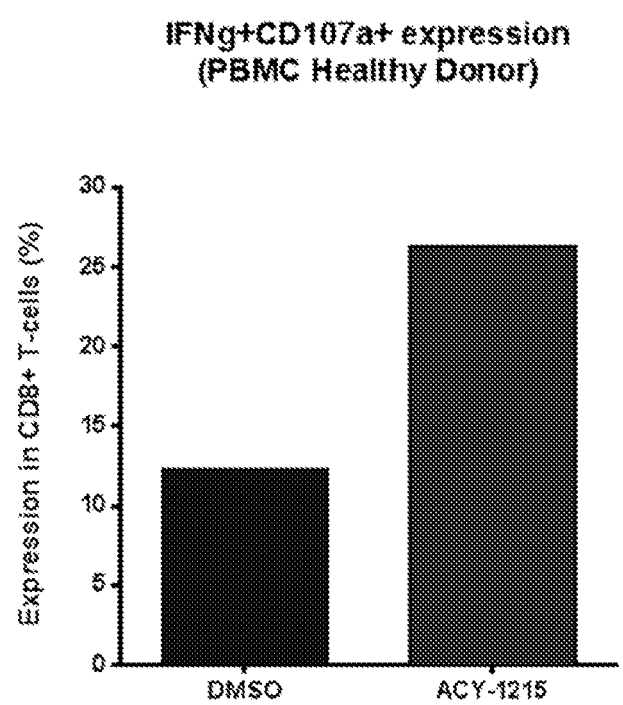
Figure 9A:
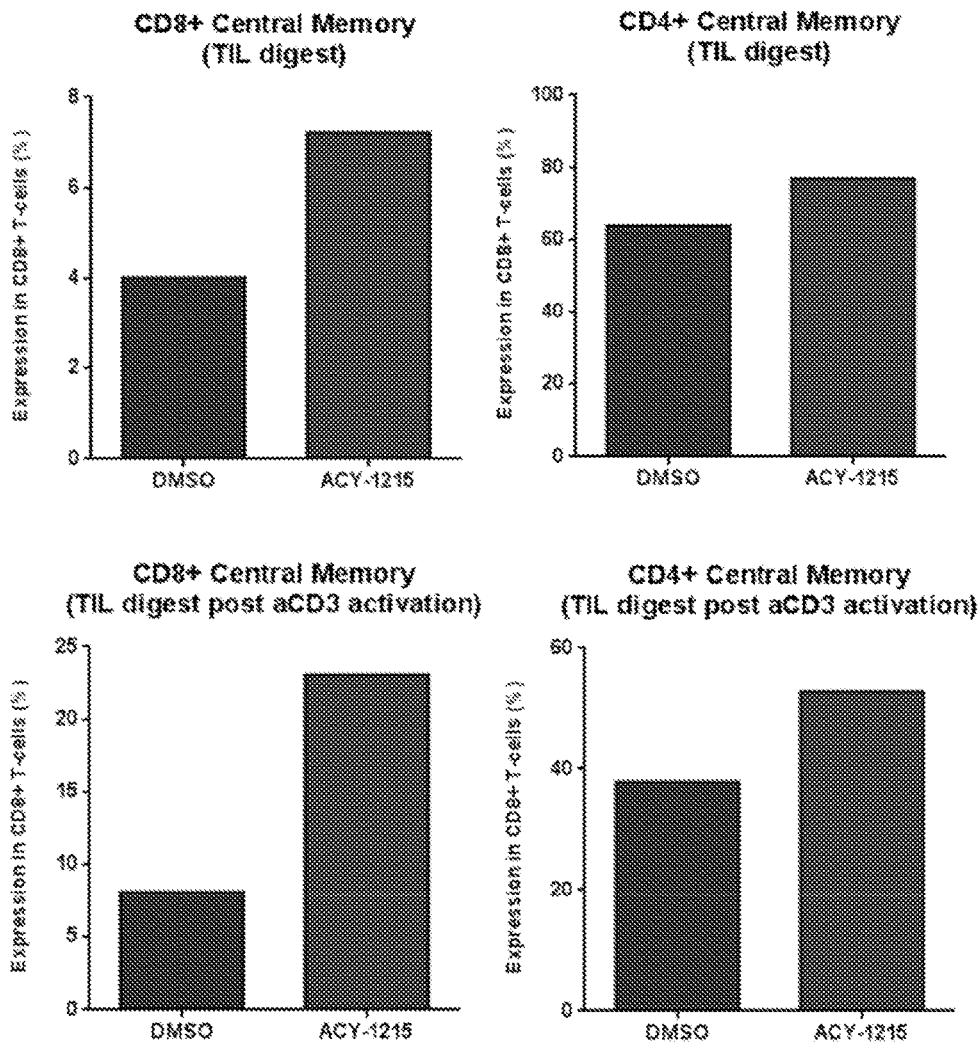
FIG. 9. HDAC6-selective inhibition increases central memory phenotype in melanoma infiltrating T lymphocytes. Frozen tumor infiltrating lymphocytes (TILs) from melanoma patients were thawed and evaluated for expression of the memory markers CD45RO, CD45RA and/or CD62L by flow cytometry. (a) Tumor digest with TILs were treated once with ACY-1215 and cultured in the presence of IL-2. Non-stimulated and aCD3-activated TILs were then assessed for memory phenotype. (b) TILs isolated from the tumor were cultured with IL-2 and evaluated for memory markers before rapid expansion protocol (Pre-REP) or (c) Post-REP.
Figure 9B:
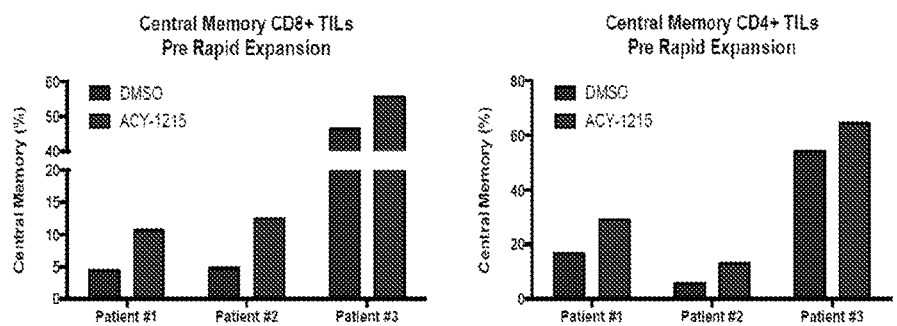
Figure 9C:
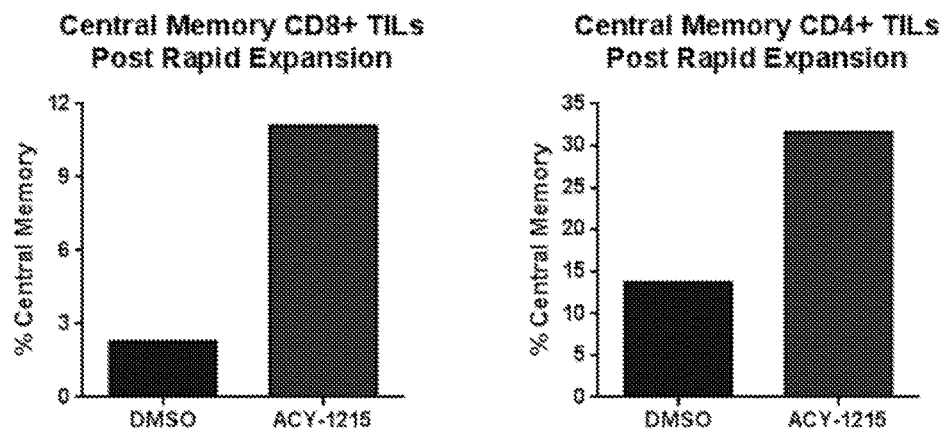
Figure 10:
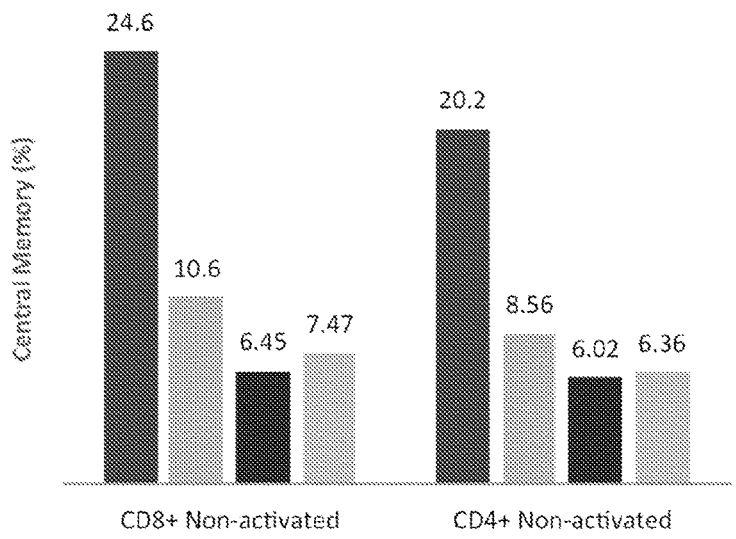
FIG. 10. Continuous HDAC6-selective inhibition robustly increases central memory phenotype in TILs. Frozen TILs were thawed, cultured in the presence of IL-2 and treated twice within two weeks with ACY-1215 or DMSO control. Cells were evaluated for expression of the memory markers CD45RO and CD62L by flow cytometry.
Figure 11A:
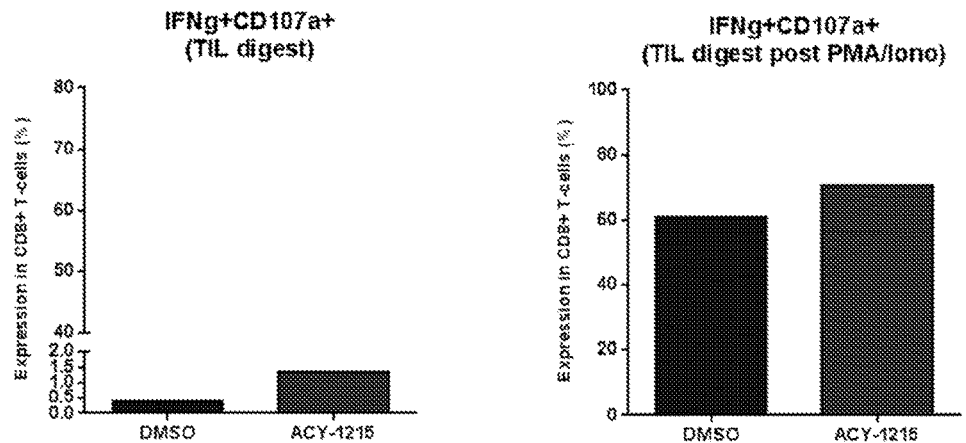
FIG. 11. HDAC6-selective inhibition improves melanoma killing capacity of TILs. All TIL samples were thawed for experiments in vitro. (a) Tumor digest and TILs were cultured with IL-2, treated once with ACY-1215 and pharmacologically activated during 6 hours for assessment of IFNg and CD107a. (b) Post-REP TILs treated twice with ACY-1215 were co-cultured in vitro with HLA-matched melanoma for 48 hours. Relative melanoma death was determined by expression of Annexin V and viability staining. (c) Pre-REP TILs and HLA-matched melanoma were co-cultured and concomitantly treated with ACY-1215 for 48 hours. Relative tumor death was assessed as above.
Figure 11B:
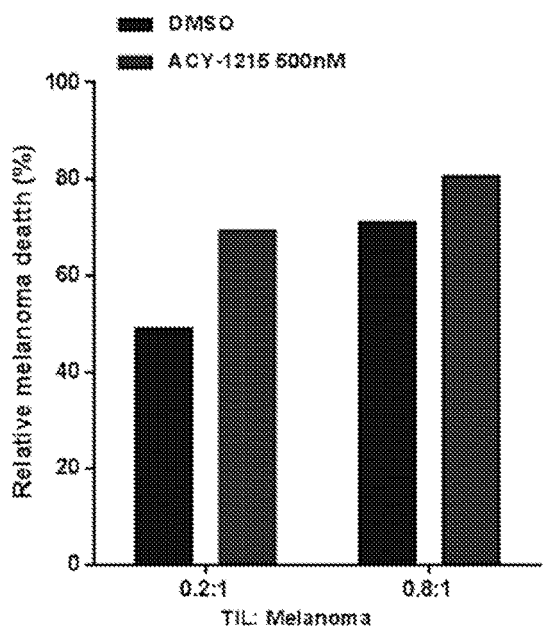
Figure 11C:
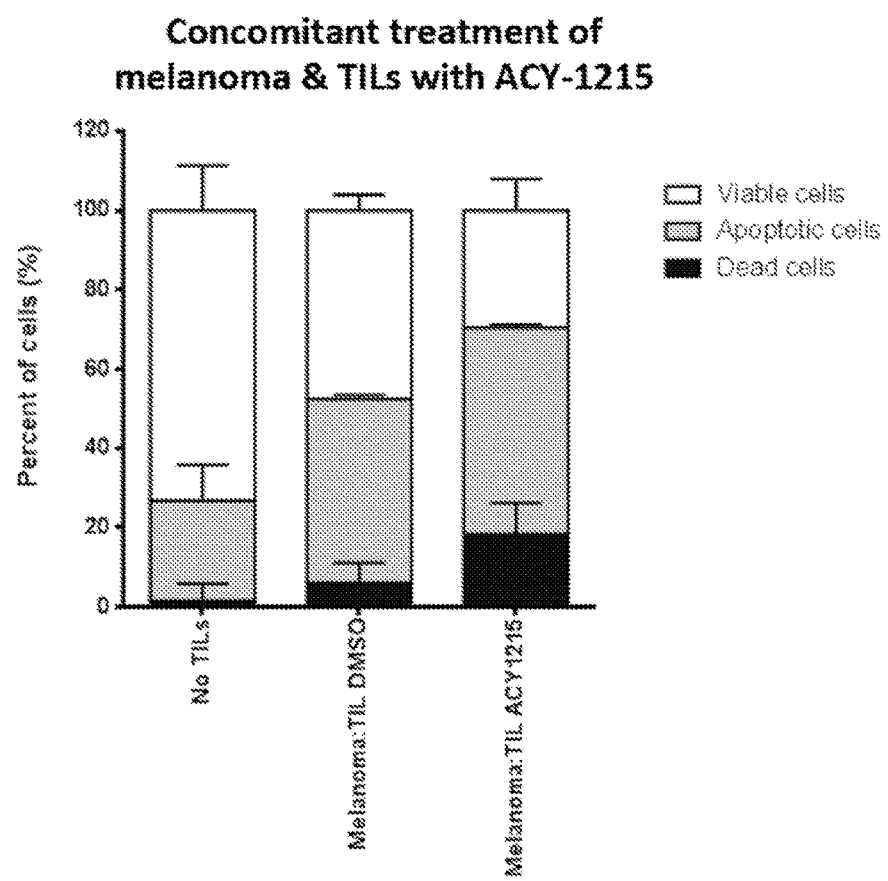
Figure 12A:
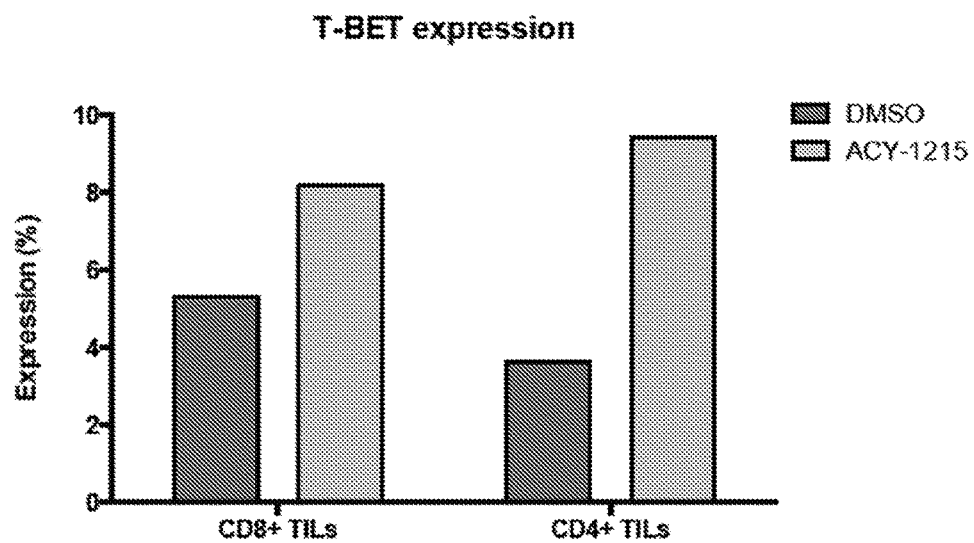
FIG. 12. HDAC6-selective inhibition alters transcription factors involved in T-cell fate. Frozen TILs were thawed, cultured with IL-2 and treated twice with ACY-1215 prior to rapid expansion (REP) in vitro. After two weeks, post-REP (a) CD8+ and (a, b) CD4+ TILs were evaluated for the expression T-BET, GATA3 and RORgT transcription factors by flow cytometry.
Figure 12B:
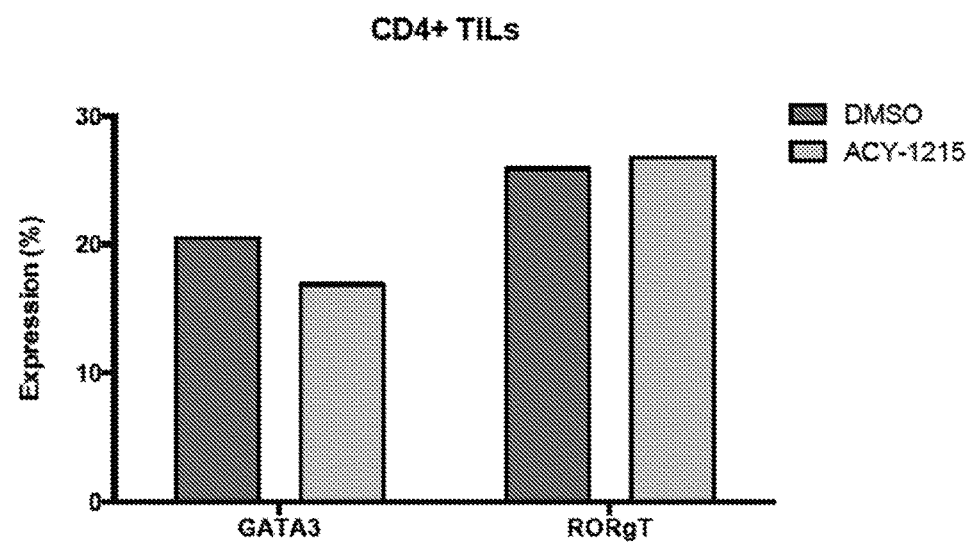

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

The term "subject" refers to any individual who is the target of administration or treatment. The subject can be a vertebrate, for example, a mammal. Thus, the subject can be a human or veterinary patient. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. The term "patient" refers to a subject under the treatment of a clinician, e.g., physician.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "increase" or other forms of the word, such as "increasing" or "increased," is meant raising the frequency or amplitude of an event or characteristic (e.g., immune response to tumor growth). It is understood that this is typically in relation to some standard or expected value, in other words it is relative, but that it is not always necessary for the standard or relative value to be referred to. For example, "increase anti-tumor response" means increasing any marker used to measure an anti-tumor immune response relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat." The term "treatment" includes the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "regression" does not necessarily imply 100% or complete regression. Rather, there are varying degrees of regression of which one of ordinary skill in the art recognizes as having a potential benefit or therapeutic effect. The term also encompasses delaying the onset of the disease, or a symptom or condition thereof.

The term "anticancer" refers to the ability to treat or control cellular proliferation and/or tumor growth at any concentration.

The term "tumor infiltrating lymphocyte" or "TIL" refers to white blood cells that have left the bloodstream and migrated into a tumor.

Reference will now be made in detail to specific aspects of the disclosed materials, compounds, compositions, articles, and methods, examples of which are illustrated in the accompanying Examples and Figures.

Methods

Disclosed herein are methods that utilize HDAC6 modulation to affect T-cell activation and response against tumor or peptide vaccine. This new role of HDAC6 is demonstrated herein in regulating anti-melanoma response and having positive implications for tumor infiltration lymphocyte (TIL) therapy.

In specific examples, disclosed herein are methods of increasing T-cell activation and response against tumor, comprising administering to a subject an amount of an HDAC6 inhibitor effective to increase T-cell activation and response against tumor in the subject. Also disclosed are methods of increasing expression of CD69 in a subject's T-cells, comprising: administering to the subject an effective amount of an HDAC6 inhibitor. Still further, disclosed are methods for ex vivo expanding tumor-infiltrating lymphocytes for use in adoptive cell therapy (ACT) comprising culturing tumor fragments from the subject in a culture medium comprising IL-2 and an HDAC6 inhibitor in an amount effective to expand tumor-infiltrating lymphocytes with enriched tumor-reactivity and specificity.

Also, disclosed are methods for treating a cancer in a subject comprising expanding tumor-infiltrating lymphocytes from a tumor fragment from the subject by culturing the tumor fragments in a culture medium comprising IL-2 and an HDAC6 inhibitor in an amount effective to expand tumor-infiltrating lymphocytes with enriched tumor-reactivity and specificity; treating the subject with nonmyeloablative lymphodepleting chemotherapy; and administering the tumor-infiltrating lymphocytes to the subject. The cancer can be a solid tumor. For example, the cancer can be selected from the group consisting of melanoma, ovarian cancer, breast cancer, and colorectal cancer. The cancer can be metastatic. The cancer can be recurrent.

In the disclosed methods, the inhibitor can be ACY1215. In other examples, the inhibitor can be ST-3-06, ST-2-92, Tubstatin A, Tubacin, Nexturastat A, Nexturastat B or any combination thereof. Further, examples of HDAC6 inhibitors that can be used herein include Pan-HDACi LAQ824 and HDAC6i ST-2-92. The HDAC6 inhibitor can also be administered with ipilimumab, revlimid, velcade, vemurafenib, ST-3-06, ST-2-92, Tubstatin A, Tubacin, or any combination thereof.

Also disclosed are methods of increasing T-cell activation and response against peptide vaccine comprising administering to a subject an effective amount of an HDAC6 inhibitor to increase T-cell activation and response against tumor or peptide vaccine in the subject. The HDAC6 inhibitor can be administered with the peptide vaccine or within a week after the subject has been administered a peptide vaccine.

Initially the relative expression of HDAC6 was evaluated in mouse and human T-cells, revealing decreased expression of this HDAC following CD3/CD28 stimulation. To demonstrate the role of HDAC6 in T-cell function, an HDAC6KO mouse model was utilized. Characterization of the T-cell compartments of the HDAC6KO mouse model showed a slight increase in CD4+ T-cell population in the lymph nodes at the expense of a decreased percentage of CD8+ T-cells. Further investigation using isotype-specific HDAC6 inhibitors showed similar results when WT T-cells were activated and treated with an HDAC6 inhibitor. In addition to this population skewing, HDAC6 inhibition led to an enhanced expression of CD69 in WT CD4+ T-cells. This result was reproduced in human CD4+ T-cells, indicating a role of HDAC6 in regulating T-cell activation.

To demonstrate HDAC6 inhibition for tumor immunotherapy, melanoma-bearing mice were adoptively transferred with T-cells activated and treated with an HDAC6 inhibitor. Ex vivo analysis of memory T-cell distribution in the lymph nodes demonstrated an increased percent of CD44+CD62L+ T-cells upon HDAC6 inhibition, suggesting a role of HDAC6 in the formation or distribution of memory CD4+ and CD8+ T-cells.

In a separate experiment, HDAC6KO mice inoculated with melanoma presented significantly delayed tumor growth, despite having normal lymphocyte compartments, when comparing to age-, sex-match wild-type (WT) mice. Additionally, in a tumor-peptide vaccination model, HDAC6KO mice displayed a remarkably reduced contraction phase in the antigen-specific CD8+ T-cell compartment when compared to WT mice after peptide vaccine administration. To further evaluate whether these in vivo responses were dependent on T-cells, WT or lympho-deficient, lymphoma-bearing mice were treated with an HDAC6 inhibitor. HDAC6 inhibition led to reduced tumor burden in WT mice, which was absent in lympho-deficient mice, highlighting the importance of lymphocytes in the aforementioned in vivo results. Thus, the role of HDAC6 in regulating immune cells during anti-tumor response appears to be more important than the previously reported role as a regulator of Treg function. The data presented demonstrate a positive effect of HDAC6 in T-cell activation, maintenance of anti-tumor response in vivo and persistence of reactive T-cells following peptide vaccination. The results herein described have revealed an unexplored role of HDAC6 with positive implications for cancer immunotherapy.

To further expand these results with a clinical application, previously frozen TILs from melanoma patients were thawed and treated with ACY-1215 during expansion in vitro. Accordingly, HDAC6 inhibition increased the percent of both CD8+ and CD4+ central memory T-cell subsets, as indicated by CD45RO, CD45RA, CCR7 and CD62L surface markers. To build upon these results, the expression of transcription factors involved in T-cell differentiation and polarization were evaluated. The transcription factor T-BET was found to be up-regulated in CD4+ and CD8+ TILs alter in vitro expansion and treatment with ACY-1215, while there was a mild decrease in expression of GATA3 and RORgT in CD4+ TILs. This data is suggestive of CD4+ TIL polarization towards a pro-inflammatory Th1 phenotype. Moreover, both CD4+ and CD8+ TILs expanded and treated with ACY-1215 displayed enhanced Ki67 expression compared to the control treatment group, indicating higher proliferative capacity as a result of HDAC6 inhibition. To address if ACY-1215 treatment could ultimately improve T-cell cytotoxicity against melanoma, TILs from one melanoma patient were treated with ACY-1215 at the same time of in vitro expansion and then co-cultured with HLA matched melanoma. Treatment of TILs with ACY-1215 resulted in 20% more killing of target cells than the control group. The data demonstrate a positive effect of HDAC6 inhibition in generating and maintaining anti-tumor and peptide vaccination responses in vivo.

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). They can also be derived or from blood if they are genetically engineered to express antitumor T cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. US 2011/0052530 relates to a method for performing adoptive cell therapy to promote cancer regression, primarily for treatment of patients suffering from metastatic melanoma, which is incorporated by reference in its entirety for these methods.

In some embodiments, nonmyeloablative lymphodepleting chemotherapy is administered to the subject prior to administering to the subject the expanded tumor-infiltrating lymphocytes. The purpose of lymphodepletion is to make room for the infused lymphocytes, in particular by eliminating regulatory T cells and other non-specific T cells which compete for homeostatic cytokines. Nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. A preferred route of administering cyclophosphamide and fludarabine is intravenously. Likewise, any suitable dose of cyclophosphamide and fludarabine can be administered. Preferably, around 40-80 mg/kg, such as around 60 mg/kg of cyclophosphamide is administered for approximately two days after which around 15-35 m g/m$^2$, such as around 25 mg/m$^2$ fludarabine is administered for around five days, particularly if the cancer is melanoma.

Preferably, expanded lymphocytes produced by the disclosed methods are administered as an intra-arterial or intravenous infusion, which preferably lasts about 30 to about 60 minutes. Other examples of routes of administration include intraperitoneal, intrathecal and intralymphatic. Likewise, any suitable dose of lymphocytes can be administered. In one embodiment, about $1\times10^{10}$ lymphocytes to about $15\times10^{10}$ lymphocytes are administered.

Experiments have shown that the addition of ACY-1215 to cultured T-cells consistently promotes expansion of both CD4+ and CD8+ central memory. These results have been repeated using both TIL and peripheral blood T-cells. Indeed, results show that multiple doses of ACY-1215 further enhance central memory accumulation over single dose. Central memory T-cells are a long-lived population of antigen-experienced cells primed for rapid response to antigen challenge. As persistence has been positively associated with patient response to tumor infiltrating lymphocyte (TIL) therapy, the expansion of central memory cells represents an approach for enhancing the clinical success of TIL therapy. The results disclosed herein provide a rationale for targeting HDAC6 to improve central memory phenotype and cytotoxicity of tumor infiltrating lymphocytes from melanoma patients.

Further provided herein are methods of treating or preventing cancer in a subject, comprising administering to the subject an effective amount of an HDAC6 inhibitor. Additionally, the method can further comprise administering an effective amount of ionizing radiation to the subject. The methods can further include administering a second compound or composition (e.g., an anticancer agent) to the subject.

The disclosed subject matter also concerns methods for treating a subject having an oncological disorder or condition. In one embodiment, an effective amount of one or more compounds or compositions disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

Compositions, Formulations and Methods of Administration

Compounds that can be administered according to the disclosed methods are HDAC6 inhibitors. The uniqueness of HDAC6 in containing two enzymatic pockets allows the development of isotype-specific small molecule inhibitors. In one preferred example, the compound is ACY1215 (also known as Rocilinostat), which has the following structure,

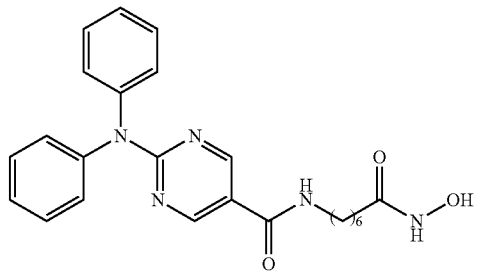

Pharmaceutically acceptable salts and hydrates of ACY1215 can also be used herein.

Other HDAC inhibitors that can be used herein include Tubacin, Tubastatin A, ST-3-06, ST-2-92, Nexturastat A, and Nexturastat B. Further examples of HDAC inhibitors that can be used include Vorinostat, LBH589, ITF2357, PXD-101, Depsipeptide, MS-275, and MGCD0103.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No.

20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib. In other aspect, the disclosed compounds are inhibitors like ACY-1215, Tubacin, Tubastatin A, ST-3-06, or ST-2-92.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Kits

The disclosed subject matter also concerns a packaged dosage formulation comprising in one or more containers at least one inhibitor compound or composition disclosed herein. A packaged dosage formulation can optionally comprise in one or more containers a pharmaceutically acceptable carrier or diluent. A packaged dosage formulation can also optionally comprise, in addition to an inhibitor compound or composition disclosed herein, other HDAC inhibitors, or an immunotherapeutic such as ipilimumab.

Depending upon the disorder or disease condition to be treated, a suitable dose(s) can be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method of increasing expression of CD69 in a subject's T-cells, comprising: administering to a subject having melanoma, ovarian cancer, breast cancer, or colorectal cancer an amount of a HDAC6 inhibitor effective to increase expression of CD69 in the subject's T-cells, wherein the HDAC6 inhibitor is selected from the group consisting of ACY1215, Tubstatin A, Tubacin, and any combination thereof.

2. The method of claim 1, wherein the inhibitor is ACY1215.

3. The method of claim 1, wherein the inhibitor is Tubstatin A, Tubacin, or any combination thereof.

4. The method of claim 1, wherein the subject is also administered ipilimumab, revlimid, velcade, vemurafenib, or any combination thereof.

5. A method for ex vivo expanding tumor-infiltrating lymphocytes for use in adoptive cell therapy, comprising: culturing tumor fragments from the subject in a culture medium comprising IL-2 and an HDAC6 inhibitor selected from the group consisting of ACY1215, Tubstatin A, Tubacin, and any combination thereof in an amount effective to expand tumor-infiltrating lymphocytes with enriched tumor-reactivity and specificity.

6. A method for treating melanoma, ovarian cancer, breast cancer, or colorectal cancer in a subject, comprising: expanding tumor-infiltrating lymphocytes from a tumor fragment from the subject by culturing the tumor fragments in a culture medium comprising IL-2 and an HDAC6 inhibitor selected from the group consisting of ACY1215, Tubstatin A, Tubacin, and any combination thereof in an amount effective to expand tumor-infiltrating lymphocytes with enriched tumor-reactivity and specificity; treating the subject with nonmyeloablative lymphodepleting chemotherapy; and administering the tumor-infiltrating lymphocytes to the subject.

7. The method of claim 1, wherein the oncological disorder is metastatic.

8. The method of claim 1, wherein the oncological disorder is recurrent.

9. The method of claim 1, wherein the subject is a human.

10. The method of claim 6, wherein the inhibitor is ACY1215.

11. The method of claim 6, wherein the inhibitor is Tubstatin A, Tubacin, or any combination thereof.

12. A method of increasing T-cell activation and response against peptide vaccine, comprising: administering to a subject an effective amount of an HDAC6 inhibitor selected from the group consisting of ACY1215, Tubstatin A, Tubacin, and any combination thereof to increase T-cell activation and response against tumor or peptide vaccine in the subject.

13. The method of claim 12, wherein the HDAC6 inhibitor is administered with the peptide vaccine.

14. The method of claim 12, wherein the HDAC6 inhibitor is administered within a week after the subject has been administered a peptide vaccine.

* * * * *